(12) United States Patent
Harder et al.

(10) Patent No.: US 6,337,142 B2
(45) Date of Patent: *Jan. 8, 2002

(54) ELONGATE ELEMENT FOR TRANSMITTING FORCES

(75) Inventors: Hans E. Harder; Harm-Iven Jensen; Andreas W. Speitling, all of New York, NY (US)

(73) Assignee: Stryker Trauma GmbH (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/102,300

(22) Filed: Jun. 22, 1998

(30) Foreign Application Priority Data

Jul. 2, 1997 (DE) .................... 297 11 559 U

(51) Int. Cl.[7] .............................. F16C 1/02; A61B 17/16
(52) U.S. Cl. .................. 428/573; 428/596; 464/183; 606/80
(58) Field of Search ................. 428/596, 573, 428/574, 575, 586; 464/183; 606/80

(56) References Cited

U.S. PATENT DOCUMENTS

| 2,515,365 A | * | 7/1950 | Zublin | 464/183 |
|---|---|---|---|---|
| 3,081,635 A | | 3/1963 | Bowers | 73/425 |
| 3,180,379 A | | 4/1965 | Stewart | 145/117 |
| 4,328,593 A | | 5/1982 | Sutter et al. | 128/92 |
| 4,390,599 A | * | 6/1983 | Broyles | 428/596 |
| 4,611,671 A | * | 9/1986 | Hansson | 173/162 H |
| 4,706,659 A | * | 11/1987 | Matthews et al. | 606/80 |
| 4,790,700 A | | 12/1988 | Schwartzman | 409/233 |
| 4,913,605 A | | 4/1990 | Schwartzman | 409/231 |
| 4,979,939 A | | 12/1990 | Shiber | 606/159 |
| 5,007,896 A | | 4/1991 | Shiber | 604/22 |
| 5,284,128 A | | 2/1994 | Hart | 128/4 |
| 5,387,218 A | * | 2/1995 | Meswania | 606/80 |
| 5,443,443 A | | 8/1995 | Shiber | 604/22 |
| 5,462,130 A | | 10/1995 | Peetz | 175/323 |
| 5,488,761 A | * | 2/1996 | Leone | 606/80 |
| 5,620,447 A | | 4/1997 | Smith et al. | 606/79 |
| 5,653,696 A | | 8/1997 | Shiber | 604/267 |
| 5,833,692 A | | 11/1998 | Cesarini et al. | 606/79 |
| 5,851,208 A | * | 12/1998 | Trott | 606/80 |
| 5,975,208 A | * | 11/1999 | Brooks | 166/313 |
| 6,053,922 A | * | 4/2000 | Krause | 606/80 |

FOREIGN PATENT DOCUMENTS

| DE | 24 42 056 A1 | 3/1977 |
|---|---|---|
| EP | 0 253 526 A1 | 1/1988 |
| EP | 0 889 252 A2 | 1/1999 |
| FR | 1280241 | 11/1961 |

* cited by examiner

Primary Examiner—John J. Zimmerman
(74) Attorney, Agent, or Firm—Lerner, David, Littenberg, Krumholz & Mentlik, LLP

(57) ABSTRACT

A hollow elongate element of elastic material for transmitting forces in which the walling comprises openings which reduce the bending resistance moment and are arranged such that the torsion resistance moment of the element essentially remains.

14 Claims, 1 Drawing Sheet

ELONGATE ELEMENT FOR TRANSMITTING FORCES

BACKGROUND OF THE INVENTION

1. Field of the Invention

The invention relates to an elongate element for transmitting forces.

2. Description of the Prior Art

In mechanics, as is known, elements are used for force transmission whose structure, shape and mounting, in addition to force transmission also effect "flexibility" (elastic deformability) in various combinations of the spacial degrees of freedom. For example a cable transmits tensile force (as a rubber cable or rubber band in an elastic manner) but not compressive force, transverse force, torsion and bending moments. A rigid beam on the other hand transmits all known forces and moments, but however with respect to the cable does not for example offer the free deformability transversely to the extension direction, thus offer e.g. the possibility of changing the transmitted tensile force in its direction by way of redirecting via a roller.

Elongate elements for transmitting forces in technical systems are used in a static or dynamic function: a shaft for example is per se a rotating, thus dynamically applied elongate element for transmitting torsional force. The already mentioned beam as part of a rod framework, for example in a scaffolding, is a statically applied elongate element which in particular transmits tensile and compressive force, but also accommodates bending moments in order to prevent buckling.

Known elongate elements for transmitting forces in various spacial directions are essentially completely rigid or "slack", but only in a few embodiment forms are of a certain desired flexibility or elasticity (stiffness). Examples of this are the rubber cable already mentioned, which in its longitudinal direction has a certain rubber elasticity and in all other directions is slack. A further example is a so-called bending shaft which elastically accommodates bending moments about any axis perpendicular to its longitudinal axis and transmits torsion force about its longitudinal axis essentially rigidly. Bendable shafts are usually wound from wire and may be coated in order to keep the wire winding in its shape. In order to transmit torsional forces in both directions, it usually requires second oppositely wound wire layers. Such bendable shafts are accordingly manufactured from several parts, but are therefore expensive in their manufacture and furthermore are of a relatively small load capacity and life expectancy.

SUMMARY OF THE INVENTION

It is the object of the present invention to provide an elongate element for transmitting forces which is elastically bendable perpendicular to its longitudinal axis at least about one axis, and which is improved with respect to its technical characteristics.

This object is achieved by a hollow elongate element of elastic material for transmitting forces wherein the wall comprises openings which reduce the bending resistance moment and are arranged such that the torsion resistance moment of the element is essentially maintained. The element for transmitting forces wherein the elongate element is cylindrical and tubular. The openings are arranged in a pattern recurrent in the longitudinal direction of the element. The element for transmitting forces, wherein the opening pattern is helical-shaped in the longitudinal direction of the element. The element for transmitting forces, wherein the openings are slots which each extend transversally into the element and of which each slot does not cut through the web region of the element, which is near to the edge, in the respective transversal cross section, and wherein the slots are formed offset to one another such that the web regions near to the edge are arranged helix-shaped in the longitudinal direction of the element.

With the present invention a hollow elongate element for transmitting forces is of elastic material. The walls of the elongate element comprises openings in an arrangement which reduce the bending resistance moment of the element. The openings in the walls of the element are arranged such that the torsion resistance moment of the element remains essentially unchanged. The element may be cylindrical, preferably tubular. It permits as a one-piece design element a simple manufacture. It requires no lubrication or regular maintenance since there are no different parts which are mounted to one another or rub against one another.

The openings may be arranged in a pattern recurrent in the longitudinal direction of the element. This is preferably spiral-shaped.

A preferred embodiment form of the invention provides slots as openings which in each case extend transversally into the elongate element. The element with a cylindrical, preferably tubular cross section is transversally notched by each slot, wherein a region near to the edge, preferably a region of the tube walls of each notched cross section is not cut through by the slot. The slots are so displaced in the circumferential direction that the regions which are not cut through are arranged in the longitudinal direction of the element in a helical manner.

In this manner the bending resistance moment of the element firstly is in each individually notched segment considerably reduced in that each slot does not cut through only one web of the tube wall. The width of the slot dependent of the depth of the slot is preferably formed larger than the tubular wall thickness. The bending resistance moment of the element about this web of a larger width than height is smallest about that axis which lies parallel to the width of the web. Because of this directional dependence of the lowest bending resistance moment of the slotted cross sections and their spiral-shaped arrangement in the longitudinal direction of the element, in the region of a rotation of the helix about the element in each bending direction there is in each case a cross section with a small bending resistance moment. By way of the fact that the helical-shaped pattern is arranged several times about the element in the longitudinal direction of the element, the element is as a whole bendable in every direction.

With each torsion-loaded component the principle tension lines run spiral-shaped about the torsional axis. By way of the fact that the openings are arranged in a pattern helical-shaped in the longitudinal direction of the element, also the webs which have not been cut through are arranged helical-shaped and form a helical-shaped uninterrupted material region which is in the position of transmitting principle torsional tensions without being weakened.

The element preferably consists of a metallic material. Due to the variety of application possibilities in surgical technology, for example as an implant for the marrow nailing of the upper arm or as a bendable shaft for a marrow space drill, the element preferably consists of biocompatible material, in particular implant steel or titanium.

Tension and compressive forces can be transmitted essentially rigidly on account of the one-pieced form of the element. By way of the dimensioning of the openings, in particular by the depth of the slots with the previously described embodiment form, the safety of the element against buckling may be set.

BRIEF DESCRIPTION OF THE DRAWINGS

Embodiment forms of the invention are hereinafter described in more detail by way of the attached drawings.

DESCRIPTION OF THE PREFERRED EMBODIMENT

Figure 1:
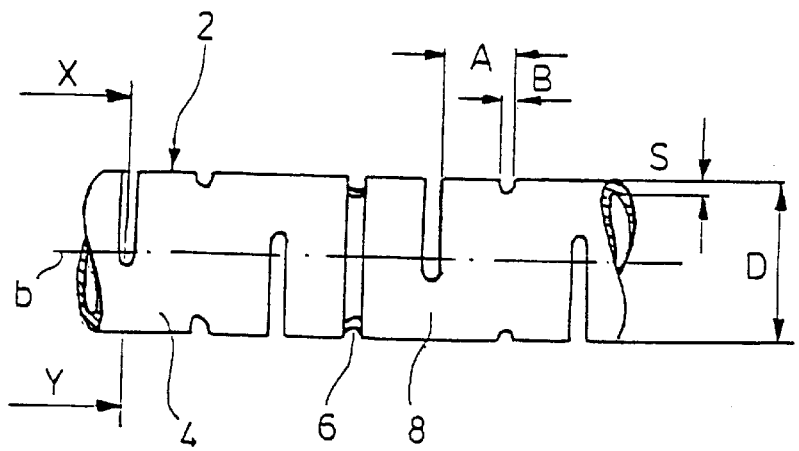
FIG. 1 shows a lateral view of a cutout of an element for transmitting forces according to the invention.
Figure 3:
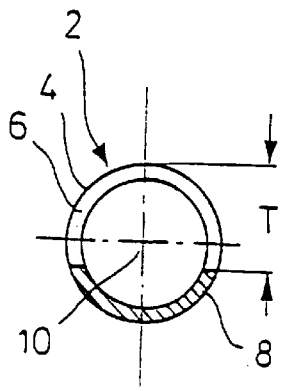
FIG. 3 shows a section along the line X-Y through the elements in FIG. 1 and 2.
Figure 2:
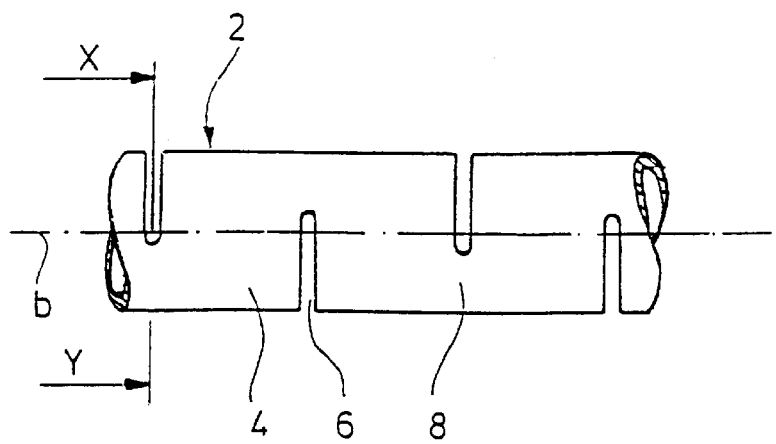
FIG. 2 shows a lateral view of a cutout of a further element for transmitting forces.

In FIGS. 1 and 2 the same details or details corresponding to one another are indicated with the same reference numerals.

With reference to FIGS. 1 and 2 an elongate element 2 for transmitting forces is formed as a tube with a tube outer diameter D and a tube thickness S. The wall 4 of the element 2 comprises slots 6 which with a width B and a depth T in each case transversally extend into the element 2. With this each slot 6 leaves a region 8 of the element, near to the edge, which is not cut through in the respective transversal cross section. The slots 6 are arranged next to one another at a distance to one another.

In FIG. 1 each slot 6b is formed displaced to the neighbouring slot at an angle of 90° about the longitudinal axis 10 of the tube. In FIG. 2 the angle is 180°. By way of this the element 2 according to FIG. 1 is bendable about two axes which lie at right angles to the longitudinal axis 10 of the element 2 as well as at right angles to one another. The element 2 according to FIG. 2 is only bendable about one axis which lies at right angles to the longitudinal axis 19 of element 2. Both elements 2 according to FIG. 1 and 2 are for example the implant for bone marrow nailing the upper arm in that on introduction into the drilled out marrow space of the upper arm bone it may follow the curvature of this bone, which is determined by the anatomy.

In order to transmit torsional, tensile and compressive force and to be bending-elastic in bending axes perpendicular to the longitudinal axis, the element 2 may be proportioned as follows: the slots 6 have a distance A to one another of >5% and <40% of the tube outer diameter D. The slots 6 have a width B of >20% and <80% of the distance A to the neighbouring slot. The slots 6 are displaced to the neighbouring slot about an angle >20° and ≦180° about the longitudinal axis 10 of the tube. Each slot 6 extends with a depth T of <90% of the tube outer diameter D transversally into the as element 2. The wall thickness S of the tubular element 2 is >5% of the tube outer diameter D.

What is claimed is:

1. An elongate element for transmitting forces during drilling of a bone marrow cavity comprising:
   a tubular body extending along a longitudinal axis, said tubular body having a plurality of slots each open to an outer diameter (D) of the tubular body and extending in a plane transversally to the longitudinal axis, said slots grouped in repeating angularly offset patterns of more than two slots, the angularly offset patterns repeating at least several times along the longitudinal extent of the tubular body each of said slots cut through a wall of said body, each of said slots spaced along said axis from adjacent slots a distance of between >5% and <40% of the tube outer diameter (D) and said more than two slots of said repeating pattern being angularly offset from adjacent slots at an angle of between 20° and <180° and connected to the adjacent slots by web regions and each of said slots extend transversely into the body with a depth (T) of <90% of the tube outer diameter (D).

2. The elongate element as set forth in claim 1 wherein said slots are angularly offset at 90° from one another.

3. The element for transmitting forces according to claim 1 wherein the slots do not cut through the web region of the body, which is near to the edge, in the respective transversal cross section, and wherein the slots are formed offset to one another such that the web regions near to the edge are arranged helix-shaped in the longitudinal direction of the element.

4. The element for transmitting forces according to claim 3 wherein the tubular body has a wall thickness (S) >5% of an outer diameter (D) of the tubular body and with a width (B) of >20% and <80% of the distance (A) to the neighboring slot.

5. The element for transmitting forces according to claim 1 wherein the body consists of a metallic material.

6. The element for transmitting forces according to claim 5 therein the body consists of steel or titanium.

7. The elongate element as set forth in claim 1 wherein the slots are angularly displaced around the tubular body at an angle >20° and <180°.

8. The elongate element as set forth in claim 7 wherein the slot width is >20% and <80% of the distance to the neighboring slot.

9. The element for transmitting forces according to claim 1 wherein the tubular has a wall thickness (S) >5% of an outer diameter (D) of the tubular body and wherein each slot is formed offset to the neighboring slot at a distance (A) of >5% and <40% of the tube outer diameter (D) and about an angle >20° and <180° about the longitudinal axis of the tubular body and extends transversely into the body with a depth (T) of <90% of the tube outer diameter (D) and with a width (B) of >20% and <80% of the distance (A) to the neighboring slot.

10. A flexible force transmitting shaft for forming an opening in the marrow cavity of a long bone comprising: a
    a tubular body for driving a marrow space drill, said tubular body extending along a longitudinal axis and having a plurality of slots open at the outer diameter (D) of the tubular body in a wall of said tubular body extending transversely to said axis, said slots grouped in repeating angularly offset patterns of more than two slots, the angularly offset patterns repeating at least several times along the longitudinal extent of the tubular body each of said slots spaced along said axis from adjacent slots a distance of between >5% and <40% of the tube outer diameter (D) and said more than two slots of said repeating pattern being angularly offset from adjacent slots around said shaft at an angle of between 20° and <180° to form a helical pattern and each of said slots extend transversely into the body with a depth (T) of <90% of the tubular outer diameter (D).

11. The flexible force transmitting shaft of claim 10 wherein the depth of each slot is less than 90% of a diameter of said tubular body.

12. The elongate element as set forth in claim 10 wherein said slots are angularly offset at 90° from one another.

13. The flexible force transmitting shaft of claim 10 wherein an uninterrupted helical web of material is formed along an outer surface of said tubular body along the longitudinal extent thereof.

14. The element for transmitting forces according to claim 10 wherein the tubular body has a wall thickness (S) >5% of an outer diameter (D) of the tubular body.

* * * * *

UNITED STATES PATENT AND TRADEMARK OFFICE
CERTIFICATE OF CORRECTION

PATENT NO.     : 6,337,142 B2
DATED          : January 8, 2002
INVENTOR(S)    : Hans E. Harder, Harm-Iven Jensen and Andreas Werner Speitling It is certified that error appears in the above-identified patent and that said Letters Patent is hereby corrected as shown below:

<u>Title page, item [75]</u>,
Line 1, after "Harder" insert -- Probsteierhagen --.
Line 1, after "Jensen" insert -- Noer --.
Line 2, after "Speitiling" insert -- Kiel --.
Line 2, cancel "New York,".
Line 2, after "of" insert -- Germany --.
Line 3, cancel "NY (US)".

<u>Column 2,</u>
Line 23, "walls" should read -- wall --.

<u>Column 3,</u>
Line 44 cancel "as".

<u>Column 4,</u>
Line 18, "therein" should read -- wherein --.
Line 36, cancel "a" (second occurrence).

Signed and Sealed this

Fourth Day of June, 2002

Attest:

Attesting Officer

JAMES E. ROGAN
*Director of the United States Patent and Trademark Office*